United States Patent [19]

Liberto et al.

[11] Patent Number: 5,168,469
[45] Date of Patent: Dec. 1, 1992

[54] THICKNESS AND FLAW DETECTION USING TIME MAPPING INTO MEMORY TECHNIQUE

[75] Inventors: Anthony J. Liberto, Huntington Beach; Robert L. Jones, Anaheim, both of Calif.

[73] Assignee: E. I. Du Pont de Nemours and Company, Wilmington, Del.

[21] Appl. No.: 636,920

[22] Filed: Jan. 2, 1991

[51] Int. Cl.[5] .............................................. G03B 42/06
[52] U.S. Cl. ......................................... 367/11; 73/606
[58] Field of Search .................... 367/99, 98, 11, 105, 367/7; 364/561, 563; 73/606, 609, 612

[56] References Cited

U.S. PATENT DOCUMENTS

| | | | |
|---|---|---|---|
| 4,365,320 | 12/1982 | Beauducel et al. | 367/21 |
| 4,890,266 | 12/1989 | Woodward | 367/99 |

Primary Examiner—Daniel T. Pihulic

[57] ABSTRACT

The invention pertains generally to ultrasonic imaging systems and is more particularly directed to use of such systems for nondestructive testing to measure the thickness of parts, or to examine parts suspected of having internal flaws but where access is often limited to the external surfaces. The invention makes thickness and flaw determinations of substantial accuracy without resulting to use of an expensive ultra high frequency clock to measure time.

1 Claim, 4 Drawing Sheets

THICKNESS AND FLAW DETECTION USING TIME MAPPING INTO MEMORY TECHNIQUE

BACKGROUND OF THE INVENTION

1. Field of Invention

The invention pertains generally to ultrasonic imaging systems and is more particularly directed to use of such systems for nondestructive testing of parts having inaccessible internal surfaces, or for parts having suspected internal flaws determinable only by access to external surfaces.

2. Description of Related Art

Nondestructive testing (NDT) relates to that science which can be used to gain information about the integrity of structures by noninvasive techniques. These systems are useful in the manufacturing and construction processes to control the quality of the work product as well as in maintenance programs to test the integrity of a workpiece in use. A typical application where NDT might be used is in the examination of welds for internal flaws or measuring thicknesses of precision parts. Aircraft, submarines and nuclear waste tanks are only a few of the areas where NDT interrogation has unquestioned utility.

The underlying principle upon which these systems are founded is a basic physics relationship: distance=velocity×time. Innocuous sound waves are used to determined the desired distance in the measured part. The velocity of sound in the material is a constant and is typically found through use of a reference book (e.g. The CRC Physics Handbook) or determined experimentally using a known good part of precision thickness. Such determinations are well known to those skilled in the art.

The time variable depends upon the thickness of the part or upon the location of the defect in the part. As sound waves travel through the part, a portion of its energy will be reflected at the interface of a discontinuity having a different refractive index. The period of time from initial transmission of the wave until the reflected energy has been detected is directly proportional to the thickness of the part, or similarly, to the location, shape, size and orientation of a defect (e.g. an air pocket) in the part.

Typically, measurements are accomplished by emitting a pulse from an ultrasonic transducer located directly on the surface of the part to be tested. Often a transmissive couplant gel is used to couple the ultrasonic pulse to the surface. Simultaneously with the generation of an ultrasonic pulse into the material to be tested, the imaging system starts a clock or counter. As, the transducer receives reflections or "echoes", the imaging system compares the level of the resultant signal to a preset threshold value. When the threshold is crossed the clock(s) or counter(s) is stopped to indicate the elapsed time T to and from a "discontinuity". Distance is then calculated by use of the equation $D = V \times T/2$.

In the case of using a clock to measure time directly, high accuracy can be obtained depending on the clock's oscillating frequency. For example a clock with a 1 GHz oscillating frequency would provide a very accurate time reading for most purposes. However, for many applications such a high frequency clock would be prohibitively expensive. It would be desirable to be able to measure time using a less expensive timing means operating at a lower frequency without incurring a substantial reduction in reading accuracy.

A major problem with using counters to determine elapsed time is that a user is never really quite sure what turned the timer off. In the prior art, a voltage threshold is employed and set to trigger when the amplitude of the reflected waveform exceeds the threshold value. (A time delay may be added to ignore possible triggering due to a reflection from the pulse's initial entry into the material.) However, it is difficult for a user to be certain that a bona fide defect has triggered cessation of the counter rather than spurious noise. Often, this uncertainty requires extensive retesting of the suspect areas.

Also, in the case of a defect, the amplitude of the reflected energy is often related to the shape, orientation and physical size of the discontinuity. As such, the user might want to know by how much the amplitude of the returning signal exceeded her preset threshold value for purposes of quality control. Multiple counters often are employed and set at various thresholds and turned on at various times of interest which require more expensive and complex circuits.

The instant invention seeks to eliminate many of these difficulties. It is an object of this invention to provide an accurate time measurement and allow the user to quickly and easily distinguish a true defect signal from random noise.

It is another object of this invention to allow the user to examine various amplitude threshold values without the need for multiple counters or redundant testing of a location.

It is a further object of this invention to provide a relatively inexpensive and low power means of measuring time that does not substantially sacrifice reading accuracy.

SUMMARY OF THE INVENTION

The instant invention comprises a method for determining the distance traveled by an ultrasonic pulse echo in a medium in order to locate a distance to a discontinuity in said medium comprising:

transmitting an ultrasonic pulse signal in said medium to produce an echo signal;

detecting said echo signal;

storing a digital representation of said echo signal in a plurality of predetermined address locations in a memory, each address location corresponding to a distance traveled by the signal in said medium;

retrieving said digital representation of said echo signal from said memory and comparing said signal with a preset reference value;

using the result of said comparison to generate a signal indicative of said distance traveled by said ultrasonic pulse echo signal in said medium.

DETAILED DESCRIPTION OF THE INVENTION

Figure 1:
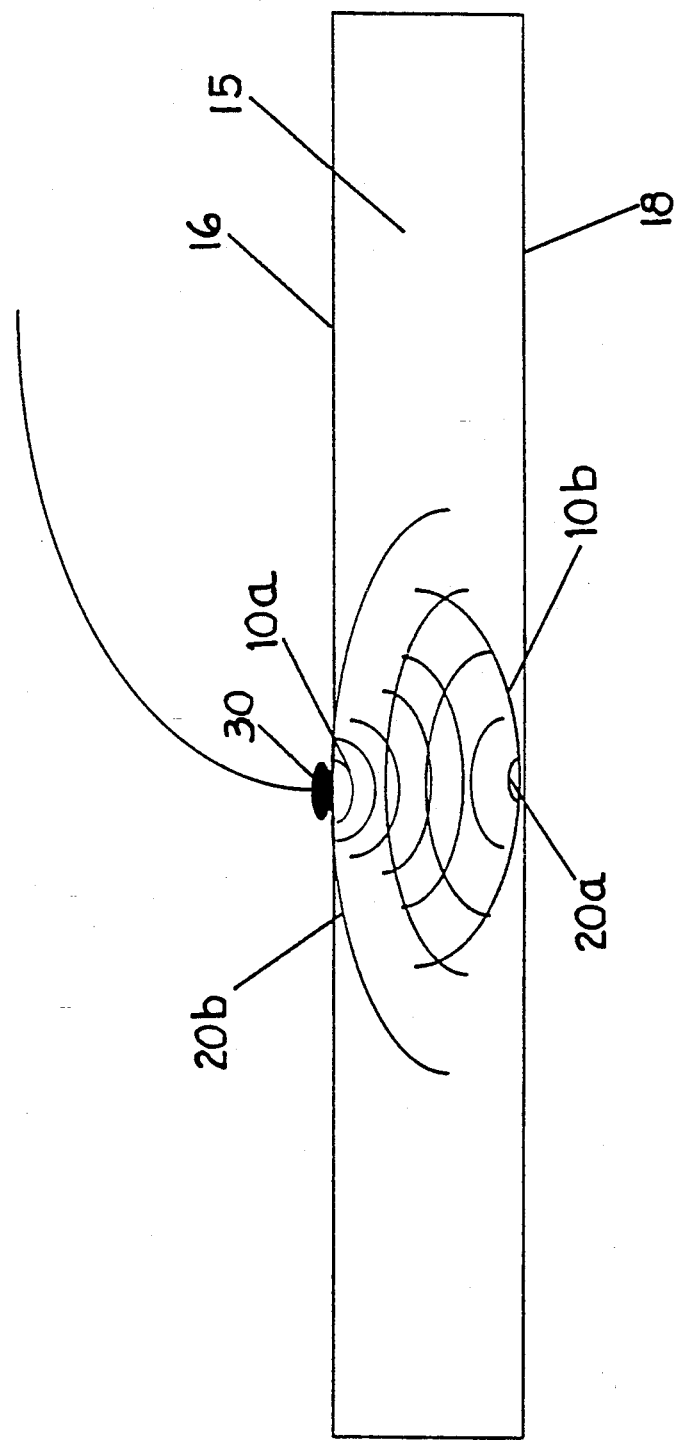
FIG. 1 depicts an ultrasonic transducer 30 that is both a transmitter and receiver of ultrasonic energy. 10a represents the initial sound wave as launched into the part medium. 10b is the sound wave just prior to echo reflection at the surface/air discontinuity. 20a is the portion of the initial sound wave that has been reflected at the discontinuity. 20b represents the sound wave just prior to reception by transducer 30.

Referring now to the drawing, an ultrasonic transducer 30 that is both a transmitter and receiver is placed on the part to be measured (FIG. 1). An ultrasonic pulse 10a of about 5 MHz is launched perpendicularly into part 15. To couple energy into part 16, a transmissive couplant gel is placed between the transducer and the part surface. The sound wave 10a then travels through the part medium until at some time T/2 later the sound wave 10b encounters a discontinuity. In FIG. 1, the discontinuity is represented by surface-to-air interface at bottom face 18 of part 15. Reflected (or echo) signal 20a propagates back through the medium of part 15 until some time T later, echo signal 20b is detected by ultrasonic transducer 30.

Figure 2:
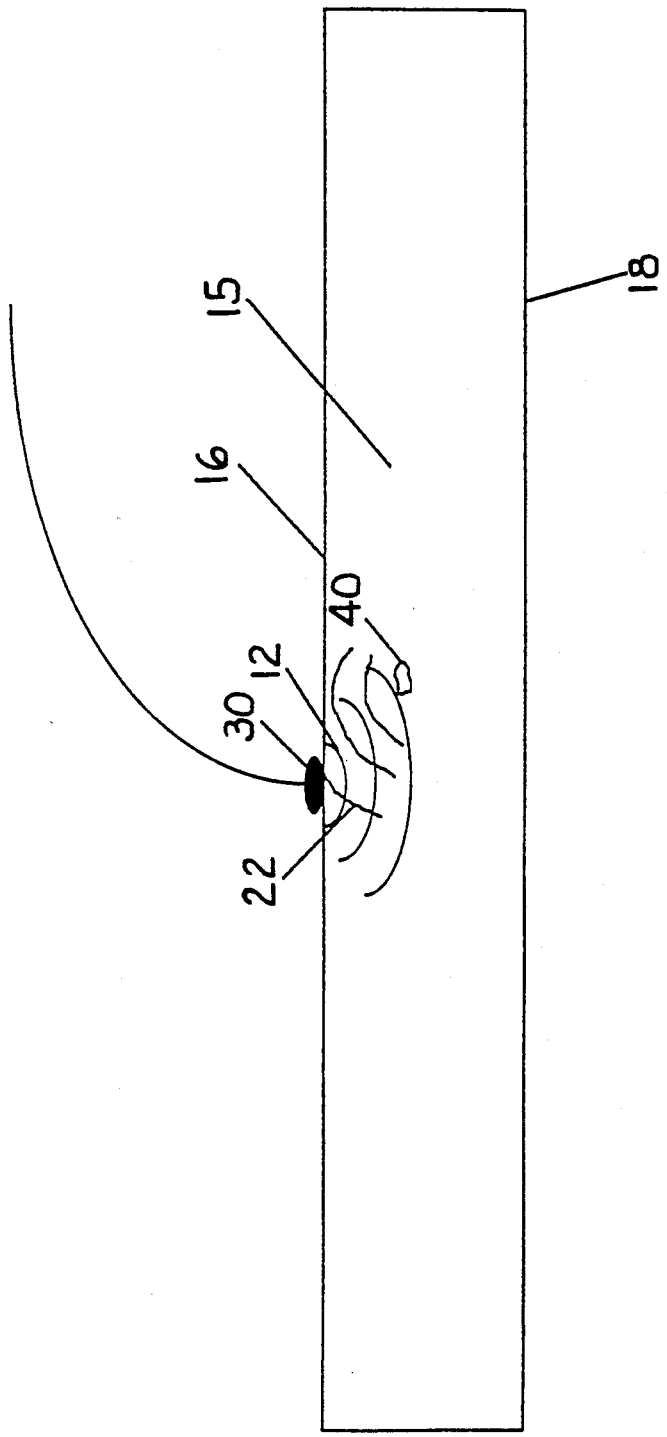
FIG. 2 shows a sound wave 12 encountering a defect 40 in the material and a portion 20 of the ultrasonic energy being reflected back and received by transducer 30.

Similarly, in FIG. 2, a discontinuity in part 15 is represented by defect 40. This defect also produces a change in the refractive index of the medium of part 15. A portion of the ultrasonic energy contained in pulse 12 will be reflected by defect 40. This echo pulse 22 will be detected by ultrasonic transducer 30.

Figure 3:
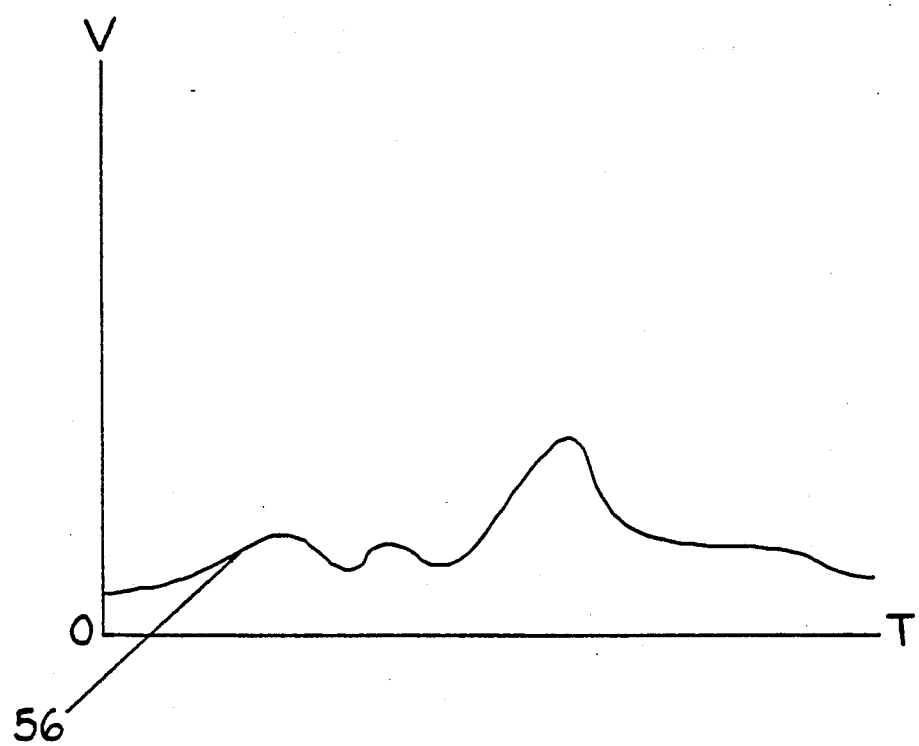
FIG. 3 is a graphical representation of the ultrasonic pulse echo 20 following detection by the transducer. This signal is digitally sampled and stored into memory.
Figure 5:
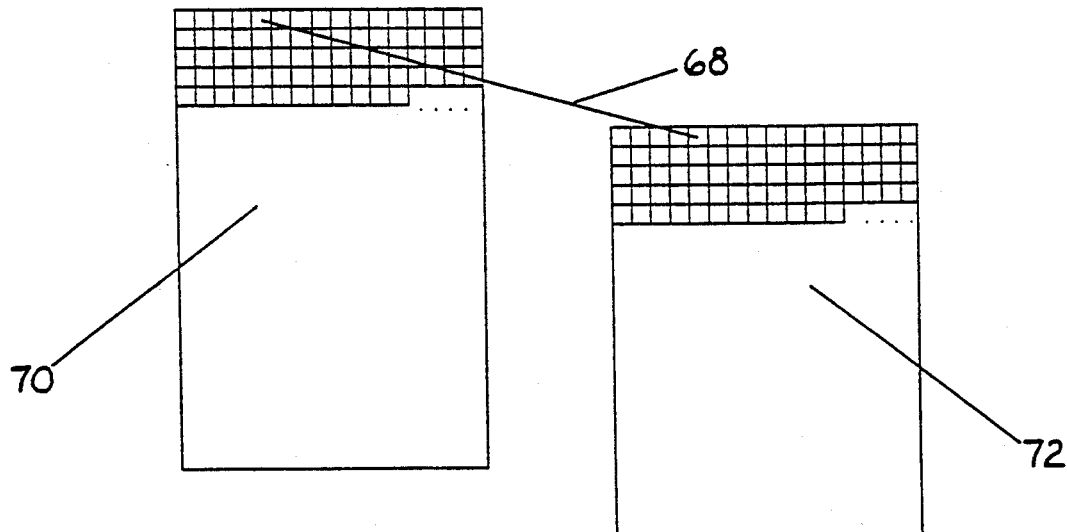
FIG. 5 depicts a section of sequentially addressable memory 70 wherein the analog signal has been digitized and stored. Each address location corresponds to a pre-stored distance value in look up table 72.

The ultrasonic echo signal received by transducer 30 is converted into an analog electrical signal (FIG. 3). This electrical signal is then digitized at about a 50 MHz sampling rate and stored in sequentially addressable memory 70 (FIG. 5). Accordingly, each successive memory location represents an additional 20 nanosecond increase in time. The Nth memory location also corresponds (via 68) to the Nth value stored in look-up table 72. The Nth value represents the distance that sound travels in the medium in N 20 nanosecond periods. So that, for example, location five in look-up table 72 represents the distance the sound has traveled in the medium in 100 nanoseconds. These distances may be precalculated and stored in look-up table for quick and convenient access.

Figure 4:
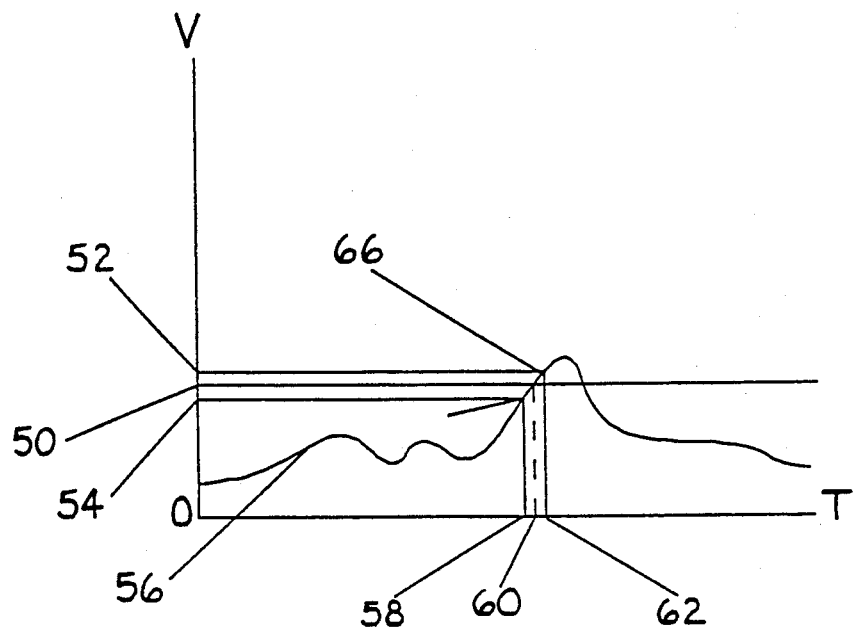
FIG. 4 is a graphical representation of digital samples 64 and 66 representing values obtained before and after the threshold value. Curve fitting techniques may be employed to make a more accurate determination of the time at which the threshold value was crossed.

After storing of the digital representation of the echo signal has begun, the content of each address location 70 is examined in chronological order of storage and compared to predetermined threshold value 50 (FIG. 4). This threshold value is set above noise level and represents a user-defined amplitude which, if exceeded, indicates a discontinuity in the material. When the value in sample address location N exceeds threshold value 50, the corresponding distance may be obtained for that address location by accessing Nth value in look-up table 72. The distance thus obtained will have a margin of error of up to 20 nanoseconds times the velocity of sound in the tested material.

Sometimes it will be necessary to obtain a distance value of greater precision and the instant method includes curve fitting and interpolation to obtain more accurate distance values.

A counter is used to keep track of the total number of sample locations N that are checked in sequentially addressable memory 70. The value at each is compared to threshold value 50. When the value in sample location N exceeds threshold value 50, this value is called the "above threshold voltage" 52 and the value immediately preceding it is called the "below threshold voltage" 54. The counter is then queried to determine the total number N of address locations examined in memory 70. Next, N is multiplied by the digital sampling rate (20 nanoseconds) to determine an "above threshold time" 62. Similarly, (N−1) is multiplied by the digital sampling rate to determine a "below threshold time" 58. It is now possible to obtain the slope of the line between below threshold point 64 and above threshold point 66.

To obtain the slope of the line between these two points, one subtracts below threshold voltage 54 from above threshold voltage 52 to obtain a resultant voltage. One then subtracts below threshold time 58 from above threshold time 62 to obtain a resultant time. (More succinctly, the resultant time difference between adjacent memory locations will be equal to the sample rate.) The resultant voltage is then divided by the resultant time to obtain the slope of the line.

Having obtained the slope of the line between the below and above threshold points (64 and 66 respectively) and, knowing reference threshold voltage 50, the unknown reference threshold time 60 from which to determine a more accurate distance to the discontinuity can be easily calculated. First, one subtracts reference threshold voltage 50 from above threshold voltage 52 to obtain a new resultant voltage. Next, one subtracts unknown reference time 60 from above threshold time 62. Then one divides the new resultant voltage by the difference between the unknown reference time 60 and above threshold time 62. One can then set this quotient equal to the slope of the line and solve the equation for unknown reference time 60. A linear approximation of the reference threshold time 60 is thus conveniently obtained.

It must be remembered that the actual time being measured is the time for the ultrasonic pulse to travel to and from the discontinuity. The resultant reference threshold time 60 must therefore be divided by two to achieve the desired time interval. Finally, the distance to the discontinuity is easily obtained by multiplying the reference threshold time by the velocity of sound in the material.

It is understood that various other curve fitting techniques well-known in the art could be employed to achieve an even more accurate solution. Use of these techniques are considered to be well within the scope of the invention as contemplated herein.

In addition, reference time values obtained from repeated measurements at the same location can be averaged to obtain a more representative time value from which to calculate the resulting distance.

Also, determining the distance to a number of defects represented by a plurality of user-defined reference threshold values does not require retesting of the part but could easily be determined by changing the reference threshold value and using the same sampled data. One counter could be incremented or decremented to suit the user's needs.

Lastly, since a digital representation of curve 56 is in memory, it can be used to display the curve and thus verify that it was, in fact, a legitimate ultrasonic pulse and not a voltage spike that exceeded the reference threshold voltage. This feature provides an additional measure of security of the reliability of the measured data.

It is understood that the specific embodiments described above are provided as examples of a preferred embodiment of the invention, but are not intended to limit the fair scope of the invention, which is defined by the appended claims.

What is claimed is:

1. In a method for acoustically testing a medium for a defect having at least a predetermined size, the method including the steps of:

transmitting an ultrasonic pulse signal to produce an echo signal;

detecting the echo signal;

sampling the detected echo signal at each of a plurality of temporally spaced points;

storing a digital representation of each sampled echo signal in a predetermined address location in a memory, each address location corresponding to a distance traveled by the signal in said medium;

the improvement comprising (a) comparing the value of each stored sample signal with a constant threshold value chosen to correspond to a defect of at least a predetermined size;

(b) identifying a first, greater, bracketing distance in the medium by identifying the stored sample signal that first exceeds the constant threshold value and the address location where that sample signal is stored;

(c) identifying a second, lesser, bracketing distance by identifying the address location immediately preceding the address location where the greater bracketing signal is stored; and (d) calculating a third distance intermediate between the first and second bracketing distances, the third distance being calculated as a linear interpolation between the first and second bracketing distances, the third distance into the medium being the distance at which a defect having the predetermined size is believed to exist.

* * * * *